(12) United States Patent
Mickens

(10) Patent No.: US 12,708,565 B2
(45) Date of Patent: Aug. 18, 2026

(54) EAR PROTECTOR DEVICE

(71) Applicant: Lucille Mickens, Roseville, MI (US)

(72) Inventor: Lucille Mickens, Roseville, MI (US)

( * ) Notice: Subject to any disclaimer, the term of this patent is extended or adjusted under 35 U.S.C. 154(b) by 116 days.

(21) Appl. No.: 18/668,412

(22) Filed: May 20, 2024

(65) Prior Publication Data

US 2024/0423841 A1 Dec. 26, 2024

Related U.S. Application Data

(60) Provisional application No. 63/523,202, filed on Jun. 26, 2023.

(51) Int. Cl.
*A61F 11/14* (2006.01)
*H04R 1/10* (2026.01)

(52) U.S. Cl.
CPC ............ *A61F 11/145* (2022.01); *H04R 1/105* (2013.01); *H04R 1/1091* (2013.01); *A61F 2250/001* (2013.01); *H04R 2420/07* (2013.01)

(58) Field of Classification Search
CPC .. A61F 11/145; A61F 11/14; A61F 2250/001; H04R 1/105; H04R 1/1091; H04R 2420/07
USPC ........................................................... 381/74
See application file for complete search history.

(56) References Cited

U.S. PATENT DOCUMENTS

| | | | | |
|---|---|---|---|---|
| 3,452,365 | A | | 7/1969 | Wallace |
| 4,660,229 | A | | 4/1987 | Harris |
| 4,682,374 | A | | 7/1987 | Geiser |
| 5,615,417 | A | | 4/1997 | Jackson |
| 5,835,609 | A | * | 11/1998 | LeGette ................. A61F 11/14 2/209 |
| 2007/0245459 | A1 | * | 10/2007 | Hillman-Schwartz ...................... A45D 44/12 2/209 |

* cited by examiner

*Primary Examiner* — Paul Kim
(74) *Attorney, Agent, or Firm* — Brennan, Manna & Diamond, LLC

(57) ABSTRACT

An ear protector device designed to provide non-invasive protection for an individual's ear against debris, water, and potential injuries, due to scissors, chemicals, and other hair treatment tools. The device includes a waterproof side forming the exterior and a non-waterproof side in contact with the ear when the device is worn. An elastic band is sewn along the periphery to allow for a snug fit around the ear, with an adjustable opening to accommodate different ear sizes. The device's single-piece construction and heat resistance provide additional safeguarding against potential burns. In some embodiments, the ear protector device includes a built-in Bluetooth speaker integrated into the inner surface, enabling users to talk or to listen to music discreetly while maintaining privacy.

18 Claims, 5 Drawing Sheets

EAR PROTECTOR DEVICE

CROSS-REFERENCE TO RELATED APPLICATION

The present application claims priority to, and the benefit of, U.S. Provisional Application No. 63/523,202, which was filed on Jun. 26, 2023, and is incorporated herein by reference in its entirety.

FIELD OF THE INVENTION

The present invention relates generally to the field of ear protection devices. More specifically, the present invention relates to a novel cover device for protecting the ear from getting burned, scissor nips, and from receiving water therein. The cover device snugly fits on and around the ear to enclose the ear and protects same from debris, water, hot rods, and scissors during hair treatment. The device can be worn during swimming, travelling, and can be disposable or reusable. The device conforms to the ear and can also include a Bluetooth speaker to connect to an electronic device. Accordingly, the present disclosure makes specific reference thereto. Nonetheless, it is to be appreciated that aspects of the present invention are also equally applicable to other like applications, devices, and methods of manufacture.

BACKGROUND

By way of background, customers often undergo hair cutting, hair treatment, and other grooming procedures in barber shops and salons. Many of these procedures involve hot irons, scissors, curling irons, hair dryers, waxes, and harsh chemicals. These tools and substances, if not handled properly during the procedure, can lead to incidents causing injuries to the ears. For example, hot irons or curling irons can accidentally come into contact with the ear, resulting in burns. These burns can be painful and may cause damage to the skin and underlying tissues. Also, there is a risk of accidentally nicking or cutting the ear of customers with scissors while trimming or cutting hair and this can lead to bleeding and discomfort. Harsh chemicals used in hair treatments or dyeing may accidentally come into contact with the ear, causing chemical burns, skin irritation, and pain. Injuries to the ear can lead to significant pain and discomfort and can affect a person's balance, leading to dizziness or vertigo.

Commonly, hairstylists while doing hair treatment and styling, try to be cautious and may cover the ears of their customers with their hand while working. However, this method is entirely inefficient and can cause accidents. People desire an ear protector device for protecting ears while the hair treatment and styling is done.

Outdoor activities like swimming and hiking also pose a separate risk to the ears. While swimming, water and debris can enter the ear canal, leading to pain, discomfort, and even ear infections. People desire ear protectors which can prevent water and debris from entering the ear canal.

Therefore, there exists a long felt need in the art for an ear protector device that covers the ear of an individual. There is also a long felt need in the art for an ear cover device that protects the ear of an individual from any injury during hair treatment and grooming. Additionally, there is a long felt need in the art of an ear cover device that prevents debris, water and more from entering the ear canal. Moreover, there is a long felt need in the art for an ear protector device that reduces ear infections or bacteria build-up inside the ear after swimming or any water activity. Further, there is a long felt need in the art for a novel ear protector device that conforms to and completely covers the ear of an individual. Furthermore, there is a long felt need in the art for an ear protector device that snugly fits around the ear and can be easily removed after use. Finally, there is a long felt need in the art for an ear protector device that prevents ear injuries often associated with barber shops and hair salons, and prevents water and chemicals from getting inside the ear during water activities and during hair treatments.

The subject matter disclosed and claimed herein, in one embodiment thereof, comprises an ear protector device to help prevent ear injuries during hair dressing and treatment, and prevents debris, water, and chemicals from getting inside the ear canal. The ear protector device features a breathable fabric construction including a waterproof exterior to prevent the passage of water therethrough, a non-waterproof inner side, an elastic band attached along a periphery of the protector device to achieve a snug fit around the ear, an opening formed by the periphery to accommodate the ear, with the elastic band being stretchable for adjusting the size of the opening when the protector device is worn to cover the ear. The cover conforms to the ear and prevents direct contact of the ear from hair treatment products, hair styling tools, scissors, debris, and water.

In this manner, the ear protector device of the present invention accomplishes all of the forgoing objectives and provides users with an ear covering device that encircles the ear and secures to allow for a comfortable and snug fit on and around the ear. The cover reduces ear infections or bacteria build-up that may pool inside the ear after swimming and prevents injuries from hot irons, styling tools, chemicals, and scissor nips. The device can be disposable or reusable and can come in different sizes.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises an ear protector device for providing non-invasive protection to an ear of an individual from debris, water, chemicals, styling tools, and injuries associated with barber shops. The ear protector device comprises a non-invasive annular cover designed to encircle the ear, a breathable fabric construction providing adequate ventilation to prevent moisture entrapment and discomfort due to heat buildup, a waterproof exterior to prevent the passage of water and chemicals therethrough, a non-waterproof inner side in contact with the ear of the user when the device is worn to cover the ear, an elastic band attached along a periphery of the protector device to achieve a snug fit around the ear, an opening formed by the periphery to accommodate the ear, with the elastic band being stretchable for adjusting the size of the opening when the protector device is worn to cover the ear.

In yet another embodiment, the ear protector device provides a good heat resistance to protect the ear from potential burns and has a thickness exceeding 700 GSM for enhanced protection against scissor nips/cuts.

In another aspect of the present invention, a method of using an ear cover device to protect the ear of a user from debris, water, and injuries associated with barber shops is described. The method comprising the steps of providing the ear cover device, the ear cover device including a waterproof exterior surface, a non-waterproof inner surface, an elastic band attached along a periphery of the cover device to achieve a snug fit around the ear, positioning the ear cover device adjacent to the ear, the elastic band has an opening oriented towards the ear, extending the elastic band to increase the size of the opening for accommodating the ear, and releasing the elastic band to conform to the shape of the ear.

In a further embodiment of the present invention, an ear protector device is disclosed. The device comprising a protective cover designed as a non-invasive annular cover for an ear of an individual to protect the ear from debris, water, styling tools, scissors, chemicals, and injuries associated with barber shops and hair salons, a built-in Bluetooth speaker integrated into the inner surface of the protective cover, the built-in Bluetooth speaker capable of wireless pairing with a handheld user device, such as a smartphone, enabling the user wearing the protective device to engage in voice communication or to listen to audio content, the integrated design of the Bluetooth speaker does not emit audio outside from the speaker, thereby preserving the user's privacy during voice calls or audio playback.

Numerous benefits and advantages of this invention will become apparent to those skilled in the art to which it pertains upon reading and understanding of the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
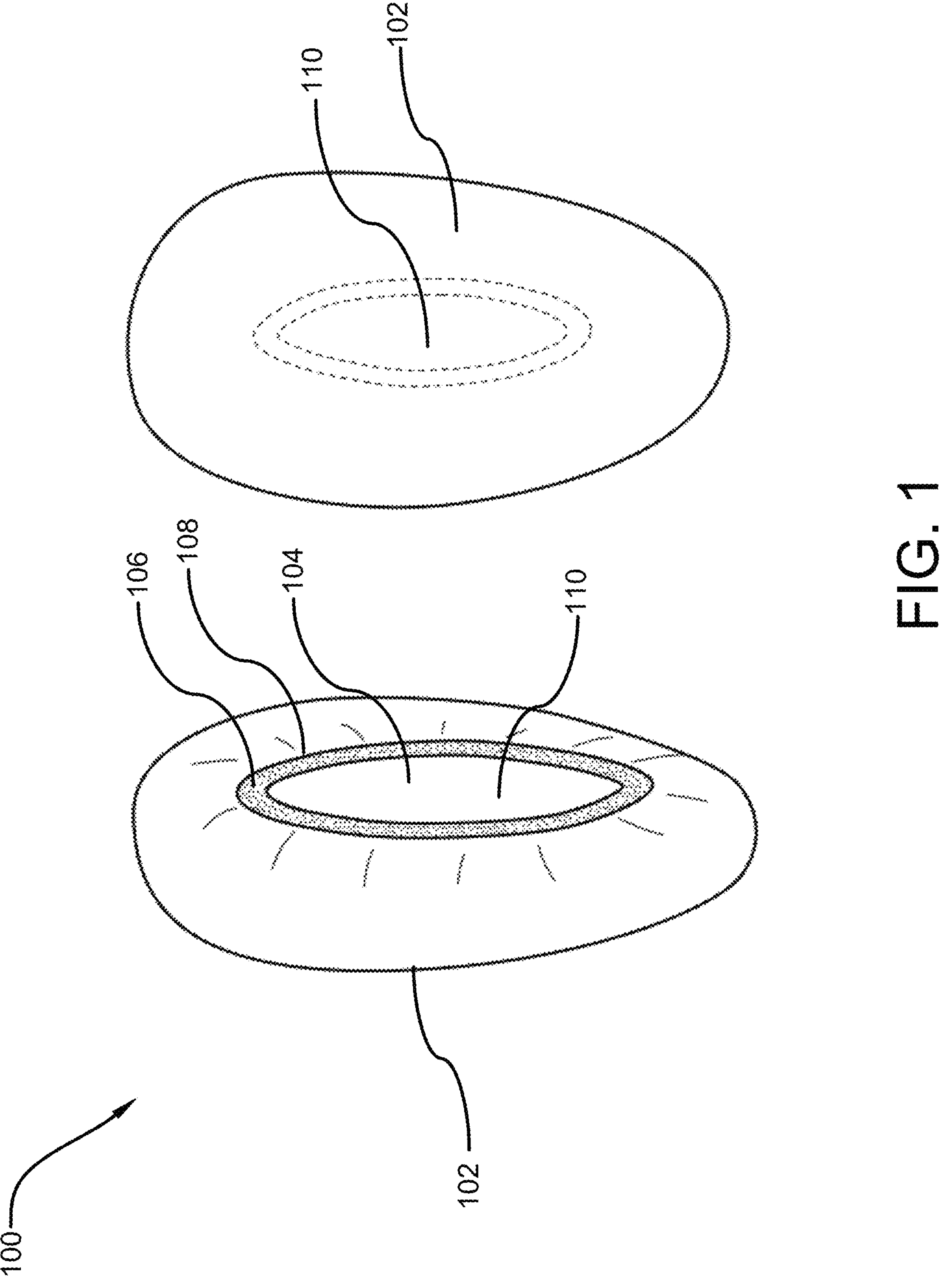
FIG. 1 illustrates a perspective view of one potential embodiment of an ear protector device of the present invention in accordance with the disclosed structure.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for an ear protector device that covers the ear of an individual. There is also a long felt need in the art for an ear cover device that protects the ear of an individual from any injury during hair treatment and grooming. Additionally, there is a long felt need in the art of an ear cover device that prevents debris, water and more from entering the ear canal. Moreover, there is a long felt need in the art for an ear protector device that reduces ear infections or bacteria build-up inside the ear after swimming or any water activity. Further, there is a long felt need in the art for a novel ear protector device that conforms to and completely covers the ear of an individual. Furthermore, there is a long felt need in the art for an ear protector device that snugly fits around the ear and can be easily removed after use. Finally, there is a long felt need in the art for an ear protector device that prevents ear injuries often associated with barber shops and hair salons, and that prevents water and chemicals from getting inside the ear during water activities.

The present invention, in one exemplary embodiment, is an ear protector device. The device comprising a protective cover designed as a non-invasive annular cover for encircling the ear of an individual, a built-in Bluetooth speaker integrated into the inner surface of the protective cover, the built-in Bluetooth speaker capable of wireless pairing with a handheld user device, such as a smartphone, enabling the user wearing the protective device to engage in voice communication or to listen to audio content, the integrated design of the Bluetooth speaker does not emit audio outside from the speaker, thereby preserving the user's privacy during voice calls or audio playback.

Figure 3:
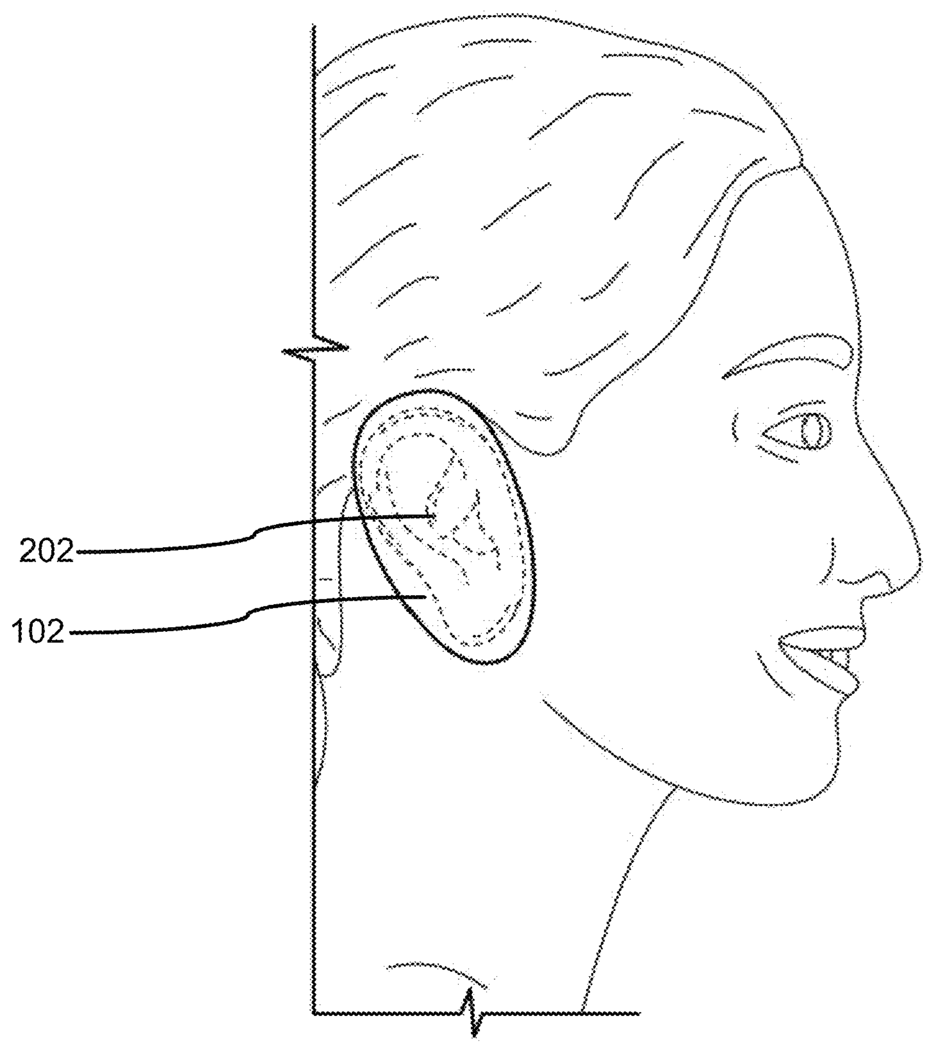
FIG. 3 illustrates a perspective view showing the ear protector device of the present invention covering an ear in accordance with the disclosed structure.

Referring initially to the drawings, FIG. 1 illustrates a perspective view of one potential embodiment of an ear protector device of the present invention in accordance with the disclosed structure. The ear protector device 100 of the present invention is designed as a non-invasive annular cover for an ear of an individual to protect the ear from debris, water, and injuries such as ear burns, scissor cuts, chemicals, and more associated with barber shops and hair salons. More specifically, the protector device 100 is made of a breathable fabric that provides adequate ventilation to avoid trapping moisture or causing discomfort due to heat buildup. The protector device 100 includes a waterproof side 102 and a non-waterproof side 104. The waterproof side 102 forms the exterior of the device 100 and prevents the water from passing therethrough. The non-waterproof side 104 touches the ear of a user when the device 100 is worn to cover the ear as illustrated in FIG. 3.

For a snug fit around the ear of a user, the device 100 has an elastic band 106 which is preferably attached along a periphery 108 of the protector device 100. The band 106 is sewn onto the periphery 108 and provides a compressible, retractable, and/or expandable length (i.e., circumference) for a snug fit around the ear. An opening 110 is formed by the periphery 108 for accommodating the ear and the elastic band 106 can be stretched as illustrated in FIG. 2 to adjust the size of the opening 110 for wearing the protector device 100 and covering the ear for protection thereof.

The waterproof side 102 can have any design, embroidery, and the like and the device 100 can come in different sizes, colors, and designs. Preferably, the device 100 can be manufactured from one or more of medical-grade silicone, neoprene, microfiber, or any other fabric. Furthermore, the device 100 has a single piece construction and provides good heat resistance to protect the ear from potential burns. The protector device 100 protects the ear from scissor nips/cuts and can have a thickness exceeding 700 grams per square meter (GSM).

Figure 2:
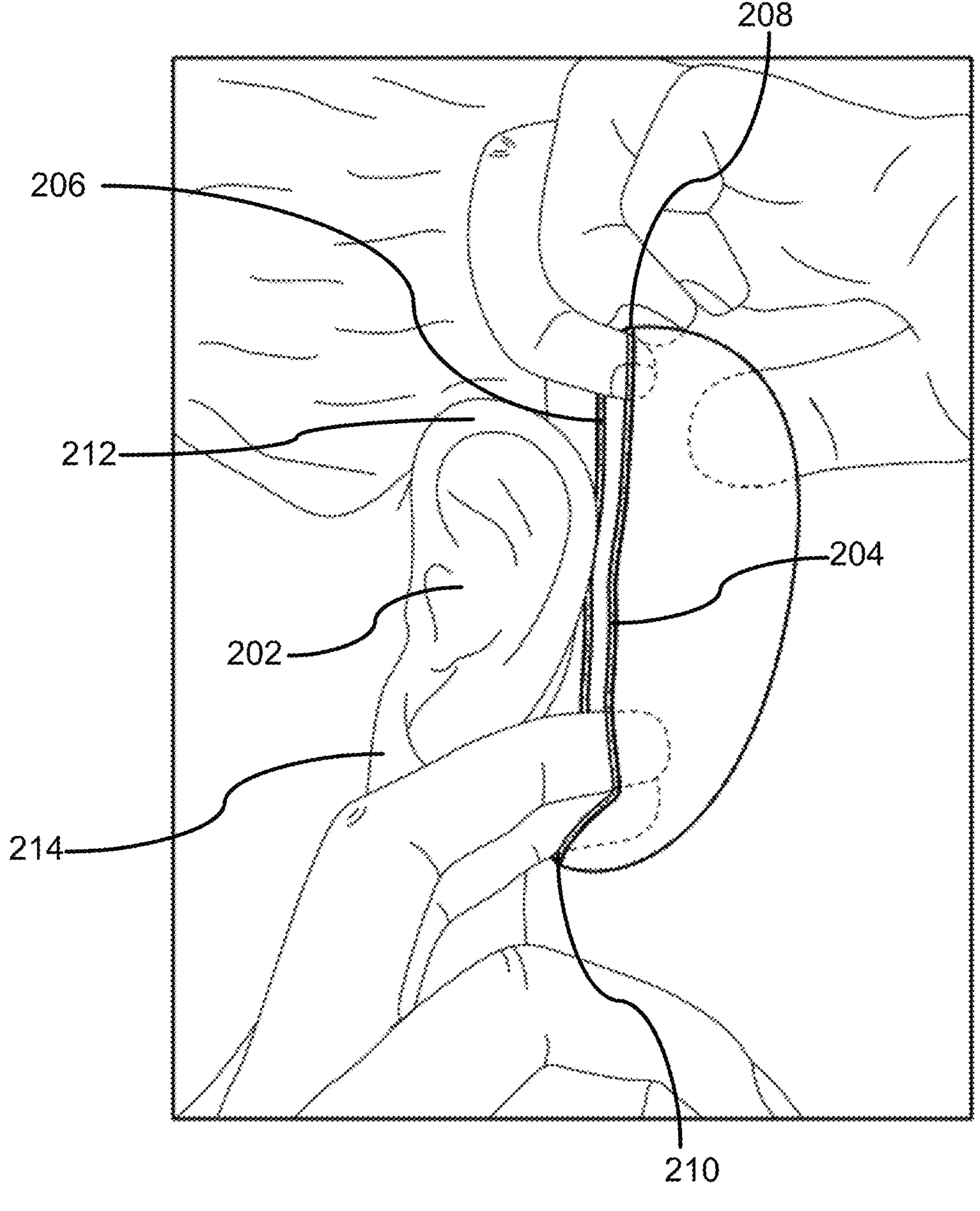
FIG. 2 illustrates an enlarged view showing a process of wearing the ear protector device of the present invention to cover the ear in accordance with the disclosed structure.

FIG. 2 illustrates an enlarged view showing a process of wearing the ear protector device of the present invention to cover the ear in accordance with the disclosed structure. For covering the ear 202, a user positions the cover device 100 adjacent to the ear 202. The elastic band 106 and the opening 110 are oriented towards the ear 202 and the elastic band 106 is extended to increase the size of the opening 110 to accommodate the ear 202. A first portion 204 of the band 106 is positioned in front of the ear 202 and the second portion 206 is positioned at the back portion of the ear 202 such that the ear 202 is enclosed by the cover 100 and the elastic band 106 snugly fits around the ear 202. The elastic band 106 is released by the user to conform to the shape and size of the ear 202.

The elastic band 106 is stretched from a first circumference to a second circumference using fingers with the top end 208 and the bottom end 210 of the band 106 stretched or pulled in opposite directions. The top end 208 is stretched beyond helix 212 of the ear 202 and the bottom end 210 is stretched below the lobe or lobule 214 of the ear 202 to enclose the ear 202 and then releasing the band 106 to conform (i.e., retract to a third circumference) to the shape of the ear 202. The band 106 forms a seal around the ear 202 and prevents water from seeping underneath the band 106 towards the ear 202. The elastic band 106 can be stretched at least to 300% (i.e., 3 times) of the original or compressed length (i.e., first circumference) and can be made of any polymer elastic.

FIG. 3 illustrates a perspective view showing the ear protector device of the present invention covering an ear in accordance with the disclosed structure. The ear protector device 100 covers the ear 202 completely to seal the ear 202 and protect the ear 202 from any potential injury in a hair salon or barber shop. The device 100 can be easily removed from the ear 202 when not required by stretching the elastic band 106. Individual ear covers can be used for covering both the ears of a user and can be independently worn and removed. In some embodiments, a user can talk on the phone while wearing the ear protector device 100. The ear protector device 100 of the present invention can be disposable or can be machine washable and reusable.

Figure 4:
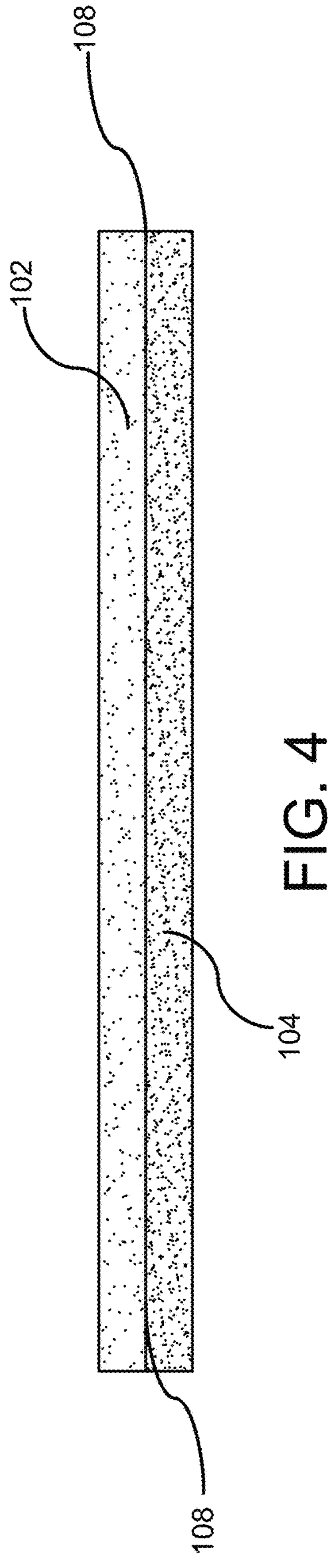
FIG. 4 illustrates a cross-sectional view of the ear cover device of the present invention in accordance with the disclosed architecture.

FIG. 4 illustrates a cross-sectional view of the ear cover device of the present invention in accordance with the disclosed architecture. The cover device 100 includes an exterior waterproof layer 102 and an inner non-waterproof layer 104. The layers 102, 104 are sewn together along the periphery 108 and are adhered to each other. In the preferred embodiment, the waterproof layer 102 has a thickness of about 2-7 mm and the non-waterproof layer 104 has a thickness of about 4-8 mm. The non-waterproof layer 104 can be made of any fabric or soft material, such as silk.

Figure 5:
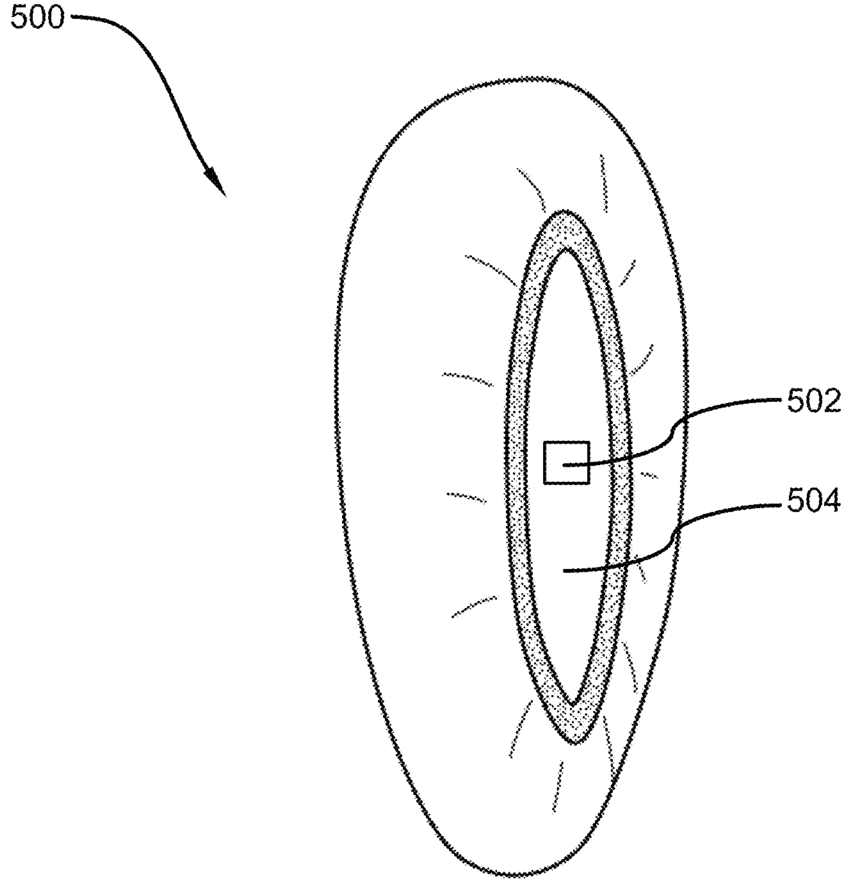
FIG. 5 illustrates a perspective view of another embodiment of the ear protector device of the present invention in accordance with the disclosed structure.

FIG. 5 illustrates a perspective view of another embodiment of the ear protector device of the present invention in accordance with the disclosed structure. In the present embodiment, the device 500 has a built-in Bluetooth speaker 502 which can be paired with a handheld user device such as a smartphone. The Bluetooth speaker 502 allows a user wearing the protective device 500 to talk or to listen to songs while wearing the device 500. The speaker 502 is integrated to the inner surface 504 and the audio from the speaker 502 does not come out of the cover 500, thus maintaining the privacy of the user.

It will be apparent to a person having skill in the art that the cover 100, 500 does not obstruct the hair treatment and trimming process while protecting the enclosed ear from any physical injury. Further, during swimming and other water activities, the cover prevents water entering the ear, thus protects the ear from any ailment.

The ear protector cover device of different embodiments of the present invention can come in individual packaging or in packages which contain, for example, 12 pairs, 24 pairs, 36 pairs, and more of the ear protector devices. The device 100, 500 is safe to use by people of all ages and genders and can be used for different purposes. The device 100, 500 is durable and cannot be easily torn using a pointed and sharp object such as scissors or a knife.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "ear cover device", "ear protector device", "cover device", "protector device", "cover", and "device" are interchangeable and refer to the ear protector device 100, 500 of the present invention.

Notwithstanding the forgoing, the ear protector device 100, 500 of the present invention can be of any suitable size and configuration as is known in the art without affecting the overall concept of the invention, provided that it accomplishes the above stated objectives. One of ordinary skill in the art will appreciate that the ear protector device 100, 500 as shown in the FIGS. 1-5 are for illustrative purposes only, and that many other sizes and shapes of the ear protector device 100, 500 are well within the scope of the present disclosure. Although the dimensions of the ear protector device 100, 500 are important design parameters for user convenience, the ear protector device 100, 500 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A protector ear covering device comprising:

an ear covering device having an exterior layer, an interior layer, and an elastic band;

wherein said exterior layer having a waterproof material;

wherein said interior layer having a breathable material;

wherein said elastic band formed around a peripheral edge of said ear covering device and defining an opening of said ear covering device;

wherein said elastic band is stretchable from a first circumference to a second circumference;

wherein said elastic band stretchable to said second circumference for placing said ear covering device over a wearer's ear;

wherein said elastic band retractable to a third circumference for securing said ear covering device around the wearer's ear;

wherein the ear covering device further comprises a medical-grade silicone; and further wherein the elastic band is sewn into the peripheral edge and forms a water-proof seal when positioned around the wearer's ear.

2. The ear covering device of claim 1, wherein said second circumference is greater than said third circumference.

3. The ear covering device of claim 2, wherein said third circumference is greater than said first circumference.

4. The ear covering device of claim 3, wherein said second circumference is at least three times greater than said first circumference.

5. The ear covering device of claim 1, wherein said ear covering device having a heat resistant material.

6. The ear covering device of claim 5, wherein said ear covering device having a material including a fabric weight of at least 700 GSM.

7. The ear covering device of claim 6, wherein said exterior layer having a thickness from 2 mm to 7 mm.

8. The ear covering device of claim 7, wherein said interior layer having a thickness from 4 mm to 8 mm.

9. The ear covering device of claim 8, wherein said interior layer having a material of silk, and further wherein said interior layer contacting the wearer's ear when said ear covering device is worn by the wearer.

10. A protector ear covering device comprising:

an ear covering device having an exterior layer, an interior layer, a Bluetooth speaker, and an elastic band;

wherein said exterior layer having a waterproof material, further wherein said exterior layer having a heat resistant material;

wherein said interior layer having a breathable material;

wherein said Bluetooth speaker attached to said interior layer;

wherein said elastic band formed around a peripheral edge of said ear covering device and defining an opening of said ear covering device;

wherein said elastic band is stretchable from a first circumference to a second circumference;

wherein said elastic band stretchable to said second circumference for placing said ear covering device over a wearer's ear; and wherein said elastic band retractable to a third circumference for securing said ear covering device around the wearer's ear;

wherein the ear covering device further comprises a microfiber; and further wherein the exterior and interior layers are sewn together along the peripheral edge and are adhered together.

11. The ear covering device of claim 10, wherein said second circumference is greater than said third circumference.

12. The ear covering device of claim 11, wherein said third circumference is greater than said first circumference.

13. The ear covering device of claim 10, wherein said ear covering device having a material including a fabric weight of at least 700 GSM.

14. A method of protecting ears, the method comprising the steps of:

providing an ear covering device having an exterior layer, an interior layer, and an elastic band, wherein said exterior layer having a waterproof material and said interior layer having a breathable material, and further wherein said elastic band formed around a peripheral edge of said ear covering device and defining an opening of said ear covering device;

stretching said elastic band from a first circumference to a second circumference;

placing said ear covering device over a wearer's ear; and releasing said elastic band, wherein said elastic band retracts from said second circumference to a third circumference for securing said ear covering device around the wearer's ear; and wherein the exterior layer is an embroidered exterior layer; and further wherein the elastic band is sewn into the peripheral edge and forms a water-proof seal when positioned around the wearer's ear.

15. The method of protecting ears of claim 14, wherein said second circumference is greater than said third circumference, and further wherein said third circumference is greater than said first circumference.

16. The method of protecting ears of claim 15, wherein said second circumference is at least three times greater than said first circumference.

17. The method of protecting ears of claim 16, wherein said ear covering device having one piece construction including one or more materials selected from a group consisting of a medical-grade silicone, a neoprene, and a microfiber, and further wherein said exterior layer having a heat resistant material.

18. The method of protecting ears of claim 17, wherein said exterior layer having a thickness from 2 mm to 7 mm, and further wherein said interior layer having a thickness from 4 mm to 8 mm.

* * * * *